US00PP32232P3

(12) United States Plant Patent
Hartman

(10) Patent No.: US PP32,232 P3
(45) Date of Patent: Sep. 22, 2020

(54) ***CALADIUM* PLANT NAMED 'RFL BRZ OF13-1082'**

(50) Latin Name: ***Caladium* X *hortulanum***
Varietal Denomination: RFL BRZ OF13-1082

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/501,042

(22) Filed: Feb. 13, 2019

(65) Prior Publication Data

US 2020/0260627 P1 Aug. 13, 2020

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/00
See application file for complete search history.

*Primary Examiner* — Anne Marie Grunberg
(74) *Attorney, Agent, or Firm* — C. A. Whealy

(57) ABSTRACT

A new and distinct cultivar of *Caladium* plant named 'RFL BRZ OF13-1082', characterized by its intermediate to tall height; upright and mounding plant habit; dense and bushy appearance; vigorous growth habit; rapid growth rate; fancy-type leaves that are mostly greyed red in color, randomly mottled with dark green flushed with greyed red-colored blotches and randomly dotted with light red-colored spots; and leaf petioles that are light greyed orange to light greyed red in color with numerous dark greenish brown-colored stippling and streaks.

5 Drawing Sheets

Figure 1:
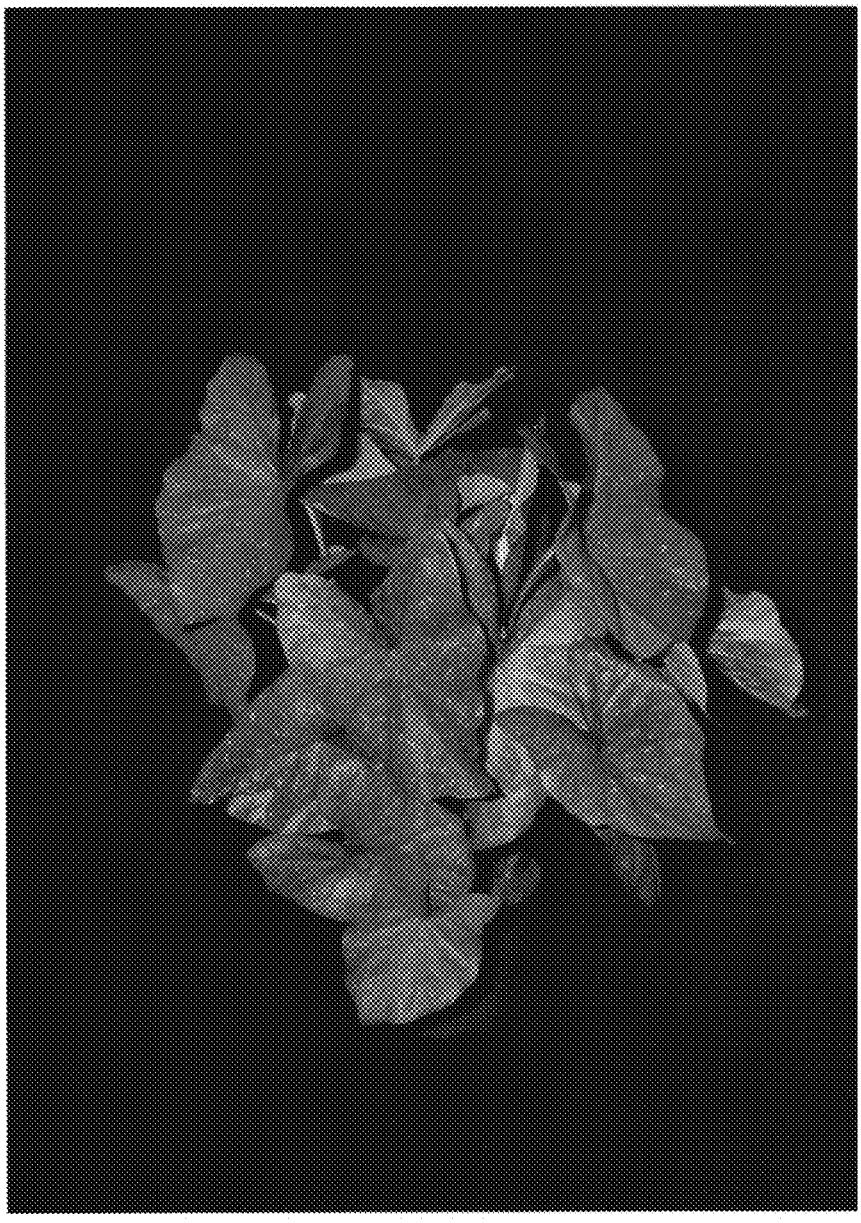

Botanical designation: *Caladium* X *hortulanum.*
Cultivar denomination: 'RFL BRZ OF13-1082'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'RFL BRZ OF13-1082'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2012 in Avon Park, Fla. of *Caladium* X *hortulanum* 'Red Flash', not patented, as the female, or seed, parent with *Caladium* X *hortulanum* 'Twist N' Shout', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2013.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2014 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'RFL BRZ OF13-1082'. These characteristics in combination distinguish 'RFL BRZ OF13-1082' as a new and distinct *Caladium* plant:

1. Intermediate to tall in height and upright and mounding plant habit; dense and bushy appearance.
2. Vigorous growth habit and rapid growth rate.
3. Fancy-type leaves that are mostly greyed red in color, randomly mottled with dark green flushed with greyed red-colored blotches and randomly dotted with light red-colored spots.
4. Petioles that are light greyed orange to light greyed red in color with numerous dark greenish brown-colored stippling and streaks.

Plants of the new *Caladium* differ primarily from plants of the female parent, 'Red Flash', in the following characteristics:

1. Plants of the new *Caladium* grow much faster than plants of 'Red Flash'.
2. Plants of the new *Caladium* and 'Red Flash' differ in leaf color as leaves of plants of the new *Caladium* are mostly greyed red in color, randomly mottled with dark green flushed with greyed red-colored blotches and randomly dotted with light red-colored spots whereas leaves of plants of 'Red Flash' have red-colored venation and interveinal areas with pink and white-colored spots and dark green-colored borders.
3. Plants of the new *Caladium* and 'Red Flash' differ in leaf petiole color as petioles of the new *Caladium* are light greyed orange to light greyed red in color with numerous dark greenish brown-colored stippling and streaks whereas petioles of plants of 'Red Flash' are red pink to tan pink in color with darker-colored stippling, stripes and tessellations.

Plants of the new *Caladium* differ primarily from plants of the male parent, 'Twist N' Shout', in the following characteristics:

1. Plants of the new *Caladium* and 'Twist N' Shout' differ in leaf color as leaves of plants of the new *Caladium* are mostly greyed red in color, randomly mottled with dark green flushed with greyed red-colored blotches and randomly dotted with light red-colored spots whereas leaves of plants of 'Twist N' Shout' are olive green in color with green to coppery bronze-colored venation and coppery orange-colored spots and blotches.
2. Plants of the new *Caladium* and 'Twist N' Shout' differ in leaf petiole color as petioles of the new *Caladium* are light greyed orange to light greyed red in color with numerous dark greenish brown-colored stippling and streaks whereas petioles of plants of 'Twist N' Shout' are light green in color.

Plants of the new *Caladium* can be compared to plants of *Caladium* X *hortulanum* 'Burning Heart', disclosed in U.S. Plant Pat. No. 27,071. In side-by-side comparisons, plants of the new *Caladium* differ primarily from plants of 'Burning Heart' in the following characteristics:

1. Plants of the new *Caladium* and 'Burning Heart' differ in leaf color as leaves of plants of the new *Caladium* are mostly greyed red in color, randomly mottled with dark green flushed with greyed red-colored blotches and randomly dotted with light red-colored spots whereas leaves of plants of 'Burning Heart' are bronze in color with contrasting salmon orange-colored spots.
2. Plants of the new *Caladium* and 'Burning Heart' differ in leaf petiole color as petioles of the new *Caladium* are light greyed orange to light greyed red in color with numerous dark greenish brown-colored stippling and streaks whereas petioles of plants of 'Burning Heart' are greyed green flushed with greyed red in color with brown-colored stippling, streaks and tessellations.

Plants of the new *Caladium* can be compared to plants of *Caladium* X *hortulanum* 'John Peed', not patented. In side-by-side comparisons, plants of the new *Caladium* differ primarily from plants of 'John Peed' in the following characteristics:

1. Plants of the new *Caladium* grow much faster than plants of 'John Peed'.
2. Plants of the new *Caladium* and 'John Peed' differ in leaf color as leaves of the new *Caladium* are mostly greyed red in color, randomly mottled with dark green flushed with greyed red-colored blotches and randomly dotted with light red-colored spots whereas leaves of 'John Peed' have dark red-colored centers and red-colored venation with dark green-colored margins.
3. Plants of the new *Caladium* and 'John Peed' differ in leaf petiole color as petioles of the new *Caladium* are light greyed orange to light greyed red in color with numerous dark greenish brown-colored stippling and streaks whereas petioles of 'John Peed' are dark pink with dark green to almost black-colored stippling and streaks.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1 of 7) is a side perspective view of a typical plant of 'RFL BRZ OF13-1082' in a container and grown in a shadehouse (tuber de-eyed).

Figure 2:
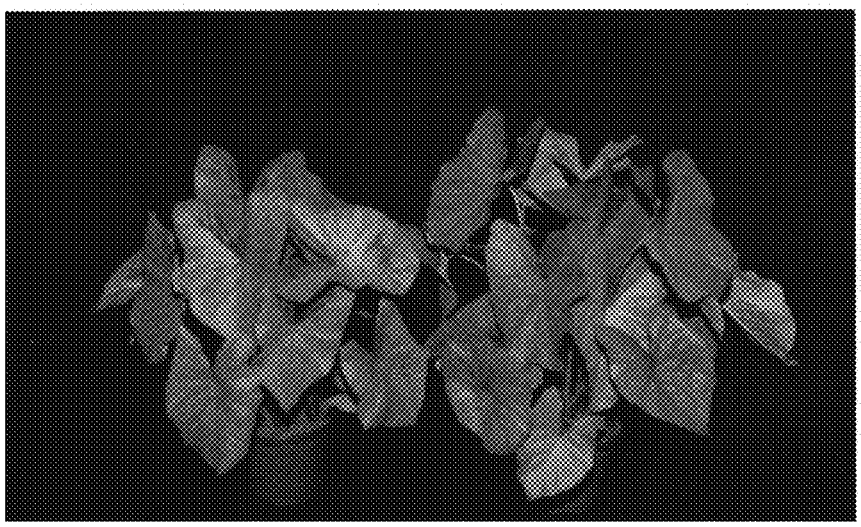

The photograph at the top of the second sheet (FIG. 2 of 7) is a comparison view of typical plants of 'RFL BRZ OF13-1082' grown in containers; the plant on the left has not had its tuber de-eyed and the plant on the right has had its tuber de-eyed prior to planting.

Figure 3:
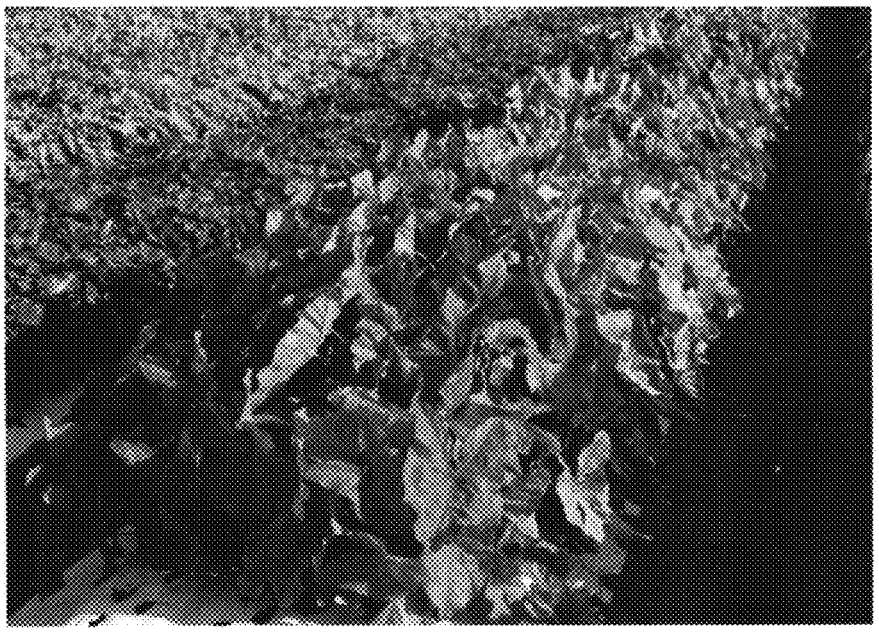

The photograph at the bottom of the second sheet (FIG. 3 of 7) is a side perspective view of typical plants of 'RFL BRZ OF13-1082' grown in an open production field.

Figure 4:
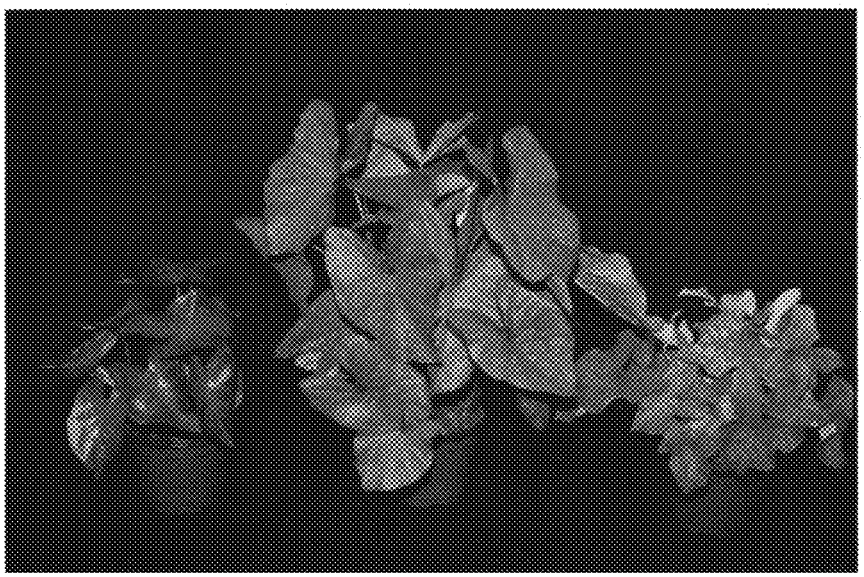

The photograph at the top of the third sheet (FIG. 4 of 7) is a comparison view of typical potted plants of the female parent, 'Red Flash' (left), 'RFL BRZ OF13-1082' (center) and the male parent, 'Twist N' Shout' (right).

Figure 5:
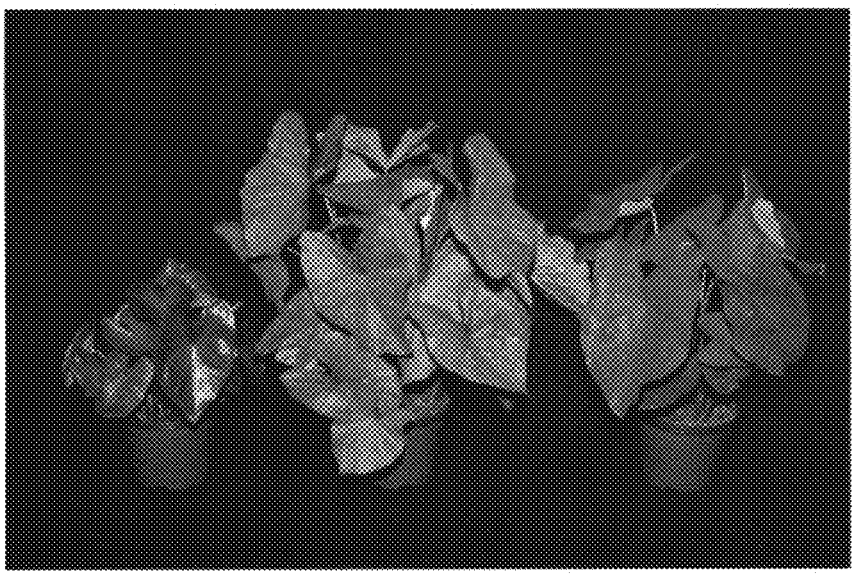

The photograph at the bottom of the third sheet (FIG. 5 of 7) is a comparison view of typical potted plants of 'John Peed' (left), 'RFL BRZ OF13-1082' (center) and 'Burning Heart' (right).

Figure 6:
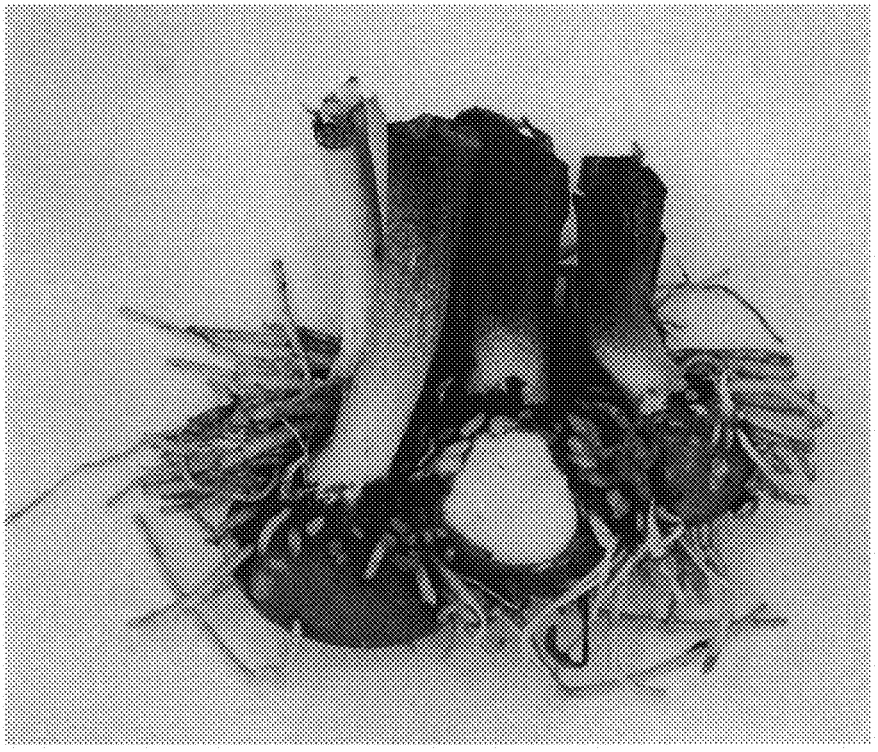

The photograph on the fourth sheet (FIG. 6 of 7) is a close-up view of typical freshly-harvested tubers with roots and leaf petioles of 'RFL BRZ OF13-1082'.

Figure 7:
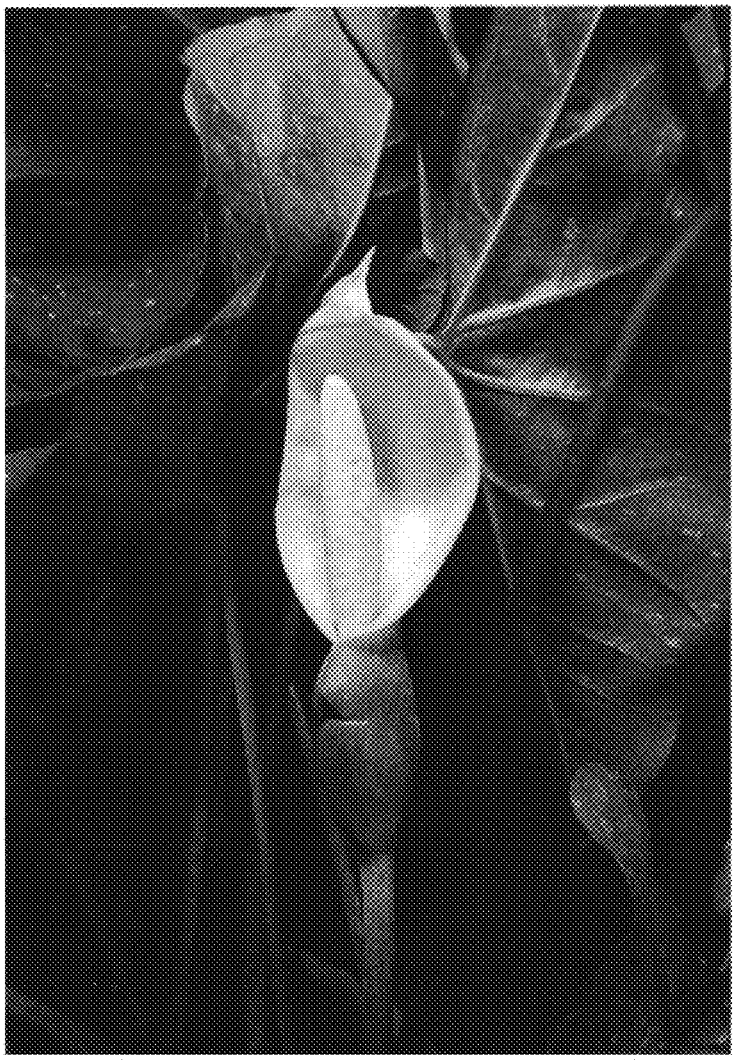

The photograph on the fifth sheet (FIG. 7 of 7) is a close-up view of a typical inflorescence of 'RFL BRZ OF13-1082'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shadehouse were seven weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'RFL BRZ OF13-1082'.

Parentage:

*Female, or seed, parent.*—*Caladium* X *hortulanum* 'Red Flash', not patented.

*Male, or pollen, parent.*—*Caladium* X *hortulanum* 'Twist N' Shout', not patented.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented; individual segments elliptic and irregular in shape. Height: About 3.7 cm to 4.4 cm. Diameter: About 6 cm to 10.7 cm. Segment height: About 2.6 cm. Segment diameter: About 2.6 cm to 3.1 cm. Axillary bud size: About 6 mm by 7 mm. Texture: Thick, starchy; somewhat brittle. Color: Epidermis, freshly-harvested: Close to N170D. Epidermis, dried: Close to 200A. Cortical tissue: Close to 4D and 8D. Axillary buds: Close to 36A to 36B. Root description: Thick, fleshy contractile roots with few lateral branches; color, close to N155D. Rooting habit: Medium density.

Plant description:

*Plant type*.—Herbaceous perennial; suitable as a potted plant in containers 15-cm to 25-cm and suitable as a landscape plant in shaded areas.

*Plant and growth habit*.—Intermediate to tall in height and upright to mounded plant habit; inverted triangle and wider than tall; dense and bushy appearance; vigorous growth habit and rapid growth rate; potted plants finish in saleable form in about six to seven weeks after planting tubers; leaf petioles and leaves arise from one or more growing points on tubers; leaf petioles initially upright and outwardly leaning with development.

*Plant height, from soil level to top of foliar plane, shadehouse-grown potted plants*.—About 35 cm to 39 cm.

*Plant height, from soil level to top of inflorescences, shadehouse-grown potted plants*.—About 34 cm.

*Plant diameter or spread, shadehouse-grown potted plants*.—About 40 cm to 45 cm.

*Number of shoots per plant, shadehouse-grown potted plants, tubers not de-eyed*.—About three to four develop per #1 tuber.

*Number of shoots per plant, shadehouse-grown potted plants, tubers de-eyed*.—About four to five develop per #1 tuber.

*Cataphylls, shadehouse-grown potted plants*.—Length: About 5.5 cm to 8.2 cm. Width: About 1.5 cm. Shape: Narrowly elliptic to lanceolate. Apex: Acute to cuspidate. Base: Sheathing the stem. Color, inner surface: Close to N155C and 182D; colors and patterns on the outer surface are visible on the inner surface. Color, outer surface: Close to N170D stippled, streaked, tessellated and flecked with close to 147A tinged with close to N200A; with development, color becoming closer to 199B and N199B stained with close to 187B.

Leaf description:

*Arrangement and type*.—Alternate; simple; fancy-type.

*Length, shadehouse-grown potted plants*.—About 21.5 cm to 30 cm.

*Width, shadehouse-grown potted plants*.—About 13.5 cm to 20 cm; when flattened, about 13.8 cm to 22 cm.

*Shape*.—Broadly ovate; flat to somewhat cupped at the center.

*Apex*.—Acute, acuminate or cuspidate.

*Base*.—Sagittate to peltate.

*Margin*.—Entire; somewhat undulate with broad undulations.

*Texture and luster, upper surface*.—Smooth, glabrous; pearlescent with a metallic sheen.

*Texture and luster, lower surface*.—Smooth, glabrous; slightly glaucous surrounding the venation with a dull sheen.

*Venation pattern*.—Pinnate.

*Color, shadehouse-grown potted plants*.—Developing and fully developed leaves, upper surface: Background color: Close to 182B tinged with close to 178A mottled with random blotches, close to 139A flushed with close to 182B tinged with close to 178A. Leaf edge: Close to 183A. Basal notch: Close to 187A. Midvein and primary venation: Close to 46A and 96A tinged with close to 183A; areas surrounding the venation, close to N34C. Random spots: Close to 39C. Developing and fully developed leaves, lower surface: Background color: Close to 189A or 191A tinged with close to 189A and flushed overall with close to 182B to 182C. Leaf edge: Close to N186C. Basal notch: Close to 187A. Midvein: Close to 181C to 181D. Primary veins: Close to 196A tinged with close to 182D. Random spots: Close to 181D.

*Petioles*.—Aspect: Initially upright and straight and outwardly leaning with development; flexible. Length, shadehouse-grown potted plants: About 21 cm to 30.2 cm. Diameter, distally, shadehouse-grown potted plants: About 3.5 mm to 6 mm. Diameter, proximally, shadehouse-grown potted plants: About 8 mm to 11 mm. Texture and luster: Smooth, glabrous; slightly glossy. Color, shadehouse-grown potted plants, when developing and fully developed: Close to N170D and 182D densely streaked, stippled and tinged with close to 200A tinged with 147A; distally (just below leaf junction), close to 182B and 181C stippled and streaked with close to N199A. Wing length, shadehouse-grown potted plants: About 5 cm to 8 cm. Wing diameter, shadehouse-grown potted plants: About 1 cm. Texture and luster, inner and outer surfaces: Smooth, glabrous; dull to slightly glossy. Wing color, shadehouse-grown potted plants: Inner surface: Close to N155C and 182D; colors and patterns on the outer surface are visible on the inner surface. Outer surface: Close to N170D stippled, streaked and flecked with close to 147A flushed with N200A.

Inflorescence description: Inflorescences observed on eight week-old shadehouse-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with mint and camphor notes.

*Natural flowering season and flower longevity*.—Plants of the new *Caladium* typically flower during the spring and summer in central Florida; flowers develop about eight weeks after growth commences; inflorescences last about three days before fading; inflorescences persistent.

*Spathe*.—Length, overall: About 11.7 cm. Length, distal open portion: About 8 cm. Length, proximal closed portion: About 3.7 cm. Width, distal open portion: About 4.1 cm. Depth, distal open portion: About 1.5 cm. Width, at constriction: About 1.6 cm. Width, proximal closed portion: About 2.5 cm. Shape, open portion: Elliptic. Apex: Acuminate. Base: Acute. Margin: Entire; smooth; slightly recurved. Texture and luster, front surface: Smooth, glabrous; dull. Texture and luster, rear surface: Smooth, glabrous; slightly glaucous; dull. Color, front surface: Distal open portion: Close to 155C; with development, color becoming closer to 199B. Proximal closed portion: Close to 148B to 148C; towards the base, flushed and mottled with close to 187A; color does not change with development. Color, rear surface: Distal open portion: Close to 145C to 145D flushed at the center with close to 145D; color does not change with development. Proximal closed portion: Close to 147A to 147B and 146A mottled and streaked with close to 178B to 178C; color does not change with development.

*Spadix*.—Length, overall: About 9.7 cm. Length, male flower zone: About 6.3 cm. Length, sterile zone: About 1.7 cm. Length, female flower zone: About 1.7 cm. Diameter, male flower zone: About 1.2 cm. Diameter, sterile flower zone: About 7 mm. Diameter, female flower zone: About 1 cm. Shape: Columnar, spindle-shaped. Apex: Obtuse to acute. Base: Obtuse. Aspect: Upright. Color, mature, male zone: Close to 158C. Color, mature, sterile zone: Close to 155D. Color, mature, female zone: Close to 159D. Male flowers: Quantity per spadix: About 162. Shape: Obovate. Height: About 3 mm to 3.5 mm. Diameter: About 3 mm. Pollen amount: Abundant. Pollen color: Close to 4D. Female flowers: Quantity per spadix: About 174. Shape: Elliptic to obovate. Height: About 2.5 mm. Diameter: About 2.2 mm. Stigma color: Close to 159D. Ovary color: Close to 158A.

*Scape*.—Length: About 22.3 cm. Diameter: About 6 mm. Strength: Sturdy; flexible. Aspect: Mostly erect. Texture and luster: Smooth, glabrous; glossy; distally, slightly glaucous. Color: Close to N170D and 182D densely stippled and streaked with close to 200A to 200B; distally, close to N170D and.182D densely stippled and streaked with close to 200A to 200B tinged with 147B.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'RFL BRZ OF13-1082' as illustrated and described.

* * * * *